US006576784B1

(12) United States Patent
Mazur et al.

(10) Patent No.: US 6,576,784 B1
(45) Date of Patent: Jun. 10, 2003

(54) ANTIVIRAL AGENTS

(75) Inventors: Yehuda Mazur, Rehovot (IL); Gad Lavie, Tenafly, NJ (US); Daniel Meruelo, Scarborough, NY (US); David Lavie, Rehovot (IL)

(73) Assignees: Yeda Research and Development Co. Ltd., Rehovot (IL); New York University, New York City, NY (US)

( * ) Notice: Subject to any disclaimer, the term of this patent is extended or adjusted under 35 U.S.C. 154(b) by 0 days.

(21) Appl. No.: 08/068,379

(22) Filed: May 27, 1993

(51) Int. Cl.[7] .............................................. C07C 69/76
(52) U.S. Cl. ........................................ 560/53; 514/533
(58) Field of Search ............................. 560/53; 514/533

(56) References Cited

FOREIGN PATENT DOCUMENTS

| WO | 9010438 | * | 9/1990 |
| WO | 9308797 | * | 5/1993 |
| WO | WO 93/08797 | | 5/1993 |

OTHER PUBLICATIONS

Banks, H. J et al Aust. J. Chem. 29(7) 1509–21 1976.*

* cited by examiner

*Primary Examiner*—Paul J. Killos
(74) *Attorney, Agent, or Firm*—Browdy and Neimark, P.L.L.C.

(57) ABSTRACT

Novel antiviral (including antiretroviral) compounds are mono- or dicarboxylic acid esters of hypericin in which one or both of the methyl groups of hypericin are substituted by carboxylic acid ester groups of the formula $COOR^3$ in which $R^3$ is alkyl, the chain of which is optionally interrupted by one or more oxygen or sulphur atoms. $R^3$ is preferably methyl, ethyl, propyl, butyl, 2-methoxyethyl or 2-(2-methoxyethoxy)ethyl. The compounds may be formulated into pharmaceutical compositions and may be used in any manner which has previously been known for hypericin.

29 Claims, 2 Drawing Sheets

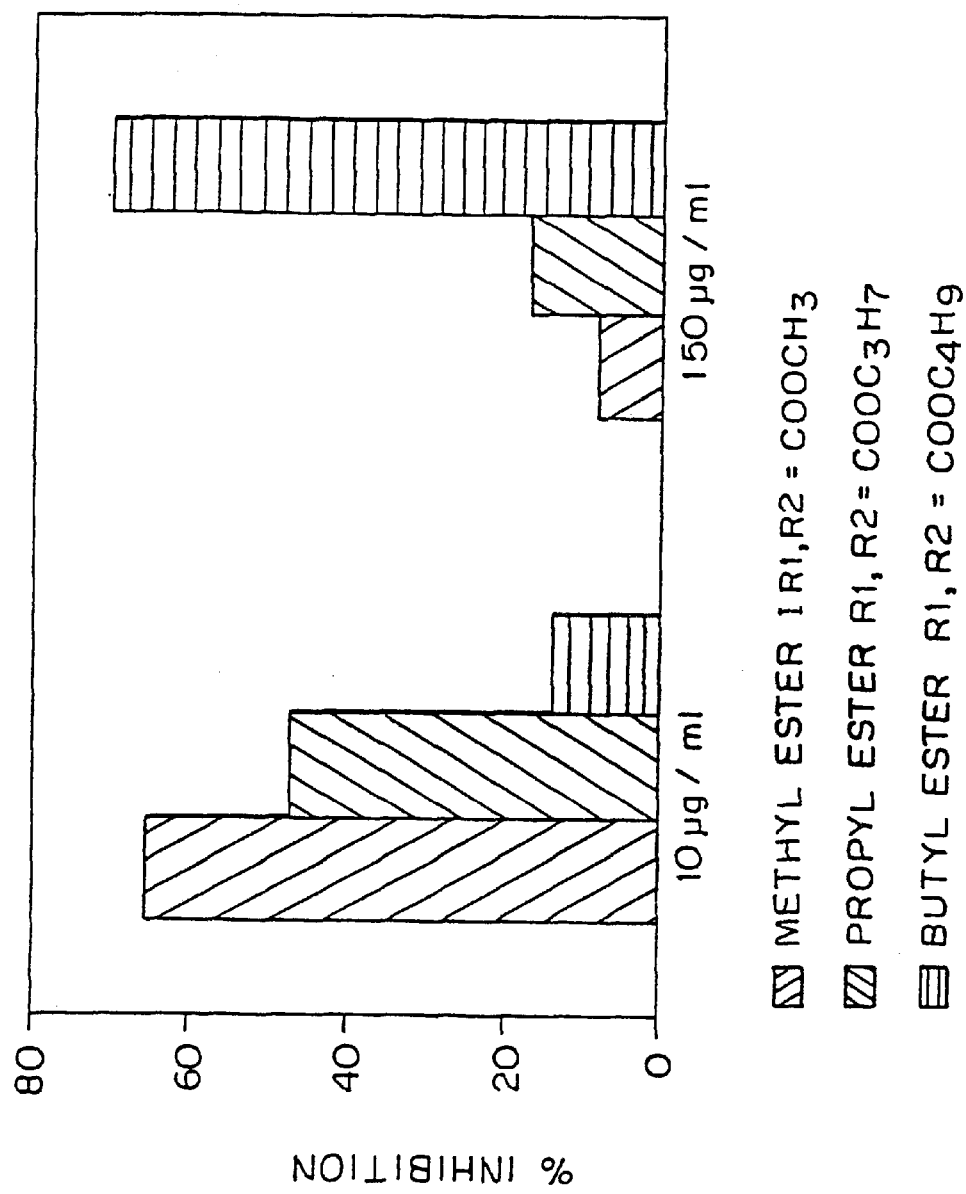

ANTIVIRAL AGENTS

FIELD OF THE INVENTION

The present invention relates to new antiviral compounds and compositions and, more particularly, to compounds which are carboxylic ester analogs of hypericin. The invention also relates to methods of use of such compounds and compositions.

BACKGROUND OF THE INVENTION

Hypericin, a constituent of plants of the genus Hypericum, has been obtained in pure form from plants (Brockman et al., *Annalen* 553:1 (1942)), and has also been totally synthesized (Brockman et al., *Chem. Ber.* 90:2480 (1957), U.S. Pat. No. 5,120,412, issued Jun. 9, 1992).

Hypericin has the following structure:

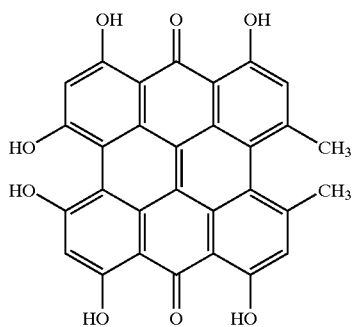

Hypericin, both from plant origin and prepared by synthesis, has been found to be a potent inhibitor of DNA and RNA containing enveloped viruses, and particularly of Human Immunodeficiency Virus (HIV), the presumed causative agent of AIDS and other conditions.

Meruelo et al., *Proc. Natl. Acad. Sci. USA* 85:5230 (1988) and U.S. Pat. No. 5,047,435 reported antiretroviral activity of hypericin and pseudohypericin in vitro and in vivo. The authors also reported that hypericin is able to inhibit HIV from infecting individual cells. U.S. Pat. No. 4,898,891, issued Feb. 6, 1990, discloses antiviral pharmaceutical compositions containing hypericin and pseudohypericin, as well as methods for using these compositions to treat viral infections.

U.S. Pat. No. 5,149,718, describes pharmaceutical formulations and methods for inactivating DNA and RNA viruses present in blood and other body fluids, more generally biological fluids. The pharmaceutical formulations include compounds structurally related to hypericin whose synthesis has been previously described in the literature.

PCT patent publication WO 90-10438 describes many compounds, many of which are analogs of hypericin, which also have antiviral activity. None of the hypericin analogs specifically disclosed therein were carboxylic acid or carboxylic acid ester analogs of hypericin in which one or both of the two methyl groups of hypericin were replaced by carboxylic acid or ester groups.

On the other hand, it has been described (G. Lavie et al, *J.N.Y. Acad. Sci.* 616:556, 1990) that a number of compounds related to hypericin possess very weak antiviral activity. These compounds include, among others, a dicarboxylic acid analog of hypericin whose two methyl groups were replaced by two carboxylic groups, and an octahydroxy analog of hypericin, whose two methyl groups are replaced by two hydroxyl groups. This publication demonstrates that not all compounds related to hypericin are active.

Thus, it is an object of the present invention to prepare other hypericin derivatives with enhanced antiviral and antiretroviral activity, and also to define the physical properties required for the above activity.

SUMMARY OF THE INVENTION

The present invention relates to novel compounds possessing naphthodianthrone skeletons whose structures are related to the structure of hypericin, in which one or both of the two methyl groups are replaced by carboxy ester groups. The present invention relates also to pharmaceutical compositions containing such compounds, and antiviral and antiretroviral methods of use thereof in significantly reducing or completely eliminating the infectivity of a virus or retrovirus that may be present in whole blood or other biological fluids, in vivo or in vitro.

It has now been discovered that certain compounds, structurally related to hypericin, are useful for the treatment and prevention of infections caused by viruses or retroviruses, and that some properties of the ester analogs may have advantages over those of hypericin. All of these new compounds bind to liposomes and produce singlet oxygen in the presence of visible light when bound to liposomes.

One aspect of the present invention comprises a method for preventing or treating a viral or retroviral infection in a mammal, comprising administering to such a mammal an effective amount of a compound selected from the group consisting of the hypericin analogs of the present invention, and mixtures thereof, wherein said compounds or mixtures are used as the sole antivirally- or antiretrovirally-active ingredients, or in conjunction with other antiviral or antiretroviral agents.

Another aspect of the present invention relates to a method for significantly reducing or completely eliminating the infectivitiy of a virus present in a retaining means for retaining a biological fluid by contacting the retaining means with an effective amount of at least one antiviral compound in accordance with the present invention.

The invention also relates to a method for significantly reducing or completely eliminating the infectivity of any virus or retrovirus which may be present on a non-biological surface after such surface has come into contact with a biological fluid contaminated with a virus or retrovirus by contacting such surface with an effective amount of at least one antiviral compound in accordance with the present invention.

The invention further relates to a method for treating a surface intended to come into contact with a biological fluid which may be infected with a virus or retrovirus in order to significantly reduce or completely eliminate the infectivity of any such virus or retrovirus which comes into contact with such surface by placing onto such surface an effective amount of at least one antiviral compound in accordance with the present invention.

Yet another aspect of the present invention comprises pharmaceutical compositions and formulations for treating or preventing viral or retroviral infections in mammals, such compositions and formulations comprising an effective amount of antiviral or antiretroviral agent, selected from the group consisting of the hypericin analogs of the present invention, and mixtures thereof, and a pharmaceutically acceptable carrier or diluent.

A further aspect of the present invention relates to an article of manufacture comprising a container for holding a biological fluid which may be contaminated with a virus and an effective amount for inactivating such virus of at least one antiviral compound in accordance with the present invention. The container for holding a biological fluid may be a blood bag, a blood vacuum storage tube, a condom, a test tube, a urine cup, etc. Indeed, any means for retaining such a biological fluid may be used. In fact any surface intended to come into contact with a biological fluid which may be contaminated with a virus or retrovirus may have an effective amount for inactivating such a virus or retrovirus of at least one antiviral compound in accordance with the present invention, such compound being present on the surface to contact the biological fluid no later than when such fluid contacts such surface.

Finally, yet another aspect of the present invention is a composition of matter including a spermicidal agent or a vaginal lubricating agent, in combination with an effective amount of at least one compound in accordance with the present invention. Any biological fluid treated with an antiviral effective amount of at least one compound in accordance with the present invention is also considered to be an aspect of the present invention.

These and other aspects of the present invention will be better understood by consideration of the following detailed description of the preferred embodiments.

BRIEF DESCRIPTION OF THE DRAWINGS

FIG. 2 shows inhibition of murine friend virus (FV) spenomegaly in mice by the methyl, propyl and butyl ester analogs of hypericin.

DETAILED DESCRIPTION OF THE INVENTION

Figure 1:
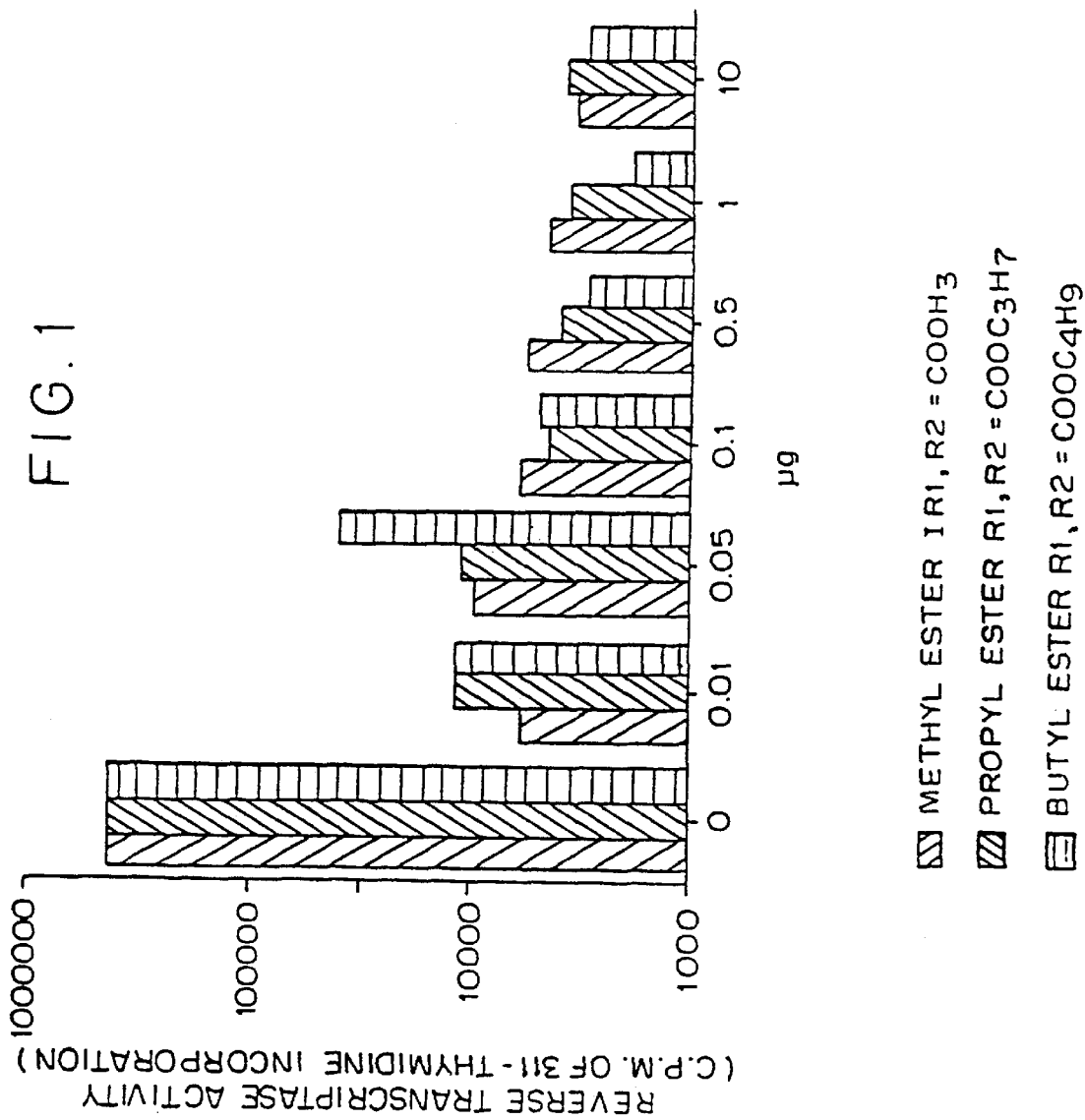
FIG. 1 shows the effects of the methyl, propyl and butyl ester analogs of hypericin on murine radiation leukemia virus (Rad LV) measured by the inhibition of virus particles-derived reverse transcriptase activity.

We have now discovered that some compounds possessing a structure related to that of hypericin and showing certain physical properties, are useful for treatment and prevention of infections caused by viruses and retroviruses, and that some properties of these molecules may have advantages over those of hypericin. These properties include the ability to bind to liposomes, and to produce singlet oxygen in visible light when bound to liposomes.

We have discovered that such compounds possess a structure of the general Formula I

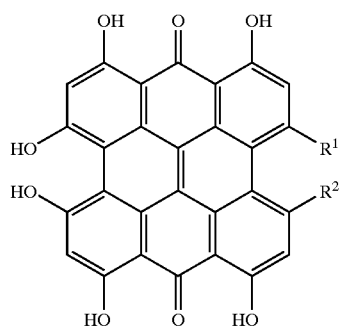

(I)

wherein one or both of $R^1$ and $R^2$ are carboxylic acid ester groups of the formula $COOR^3$ in which $R^3$ is alkyl, the chain of which is optionally interrupted by one or more oxygen or sulfur atoms. $R^3$ preferably has a total of eight or fewer carbon atoms, more preferably five or fewer, and most preferably three or fewer carbon atoms. When one of $R^1$ and $R^2$ is not a carboxylic acid ester group, it is an alkyl group, preferably a $C_{1-5}$ alkyl, and most preferably methyl.

Compounds wherein $R^1$ and $R^2$ are carboxylic acid ester groups of the formula $COOR^3$ may be prepared starting from emodic acid anthrone (CA Index Name 2-anthracenecarboxylic acid, 9,10-dihydro-4,5,7-trihydroxy-10-oxo-) described previously by H. J. Banks, *Aust. J. Chem.* 29:1509 (1976), which may be then esterified with the required alcohols. For example, compounds in which $R^3$ is methyl, n-propyl, n-butyl, 2-methoxyethyl, and 2-(2-methoxyethoxy)ethyl can be prepared from emodic acid anthrone by heating in the presence of the respective alcohols containing concentrated sulfuric acid. The obtained esters, which may be the same or different, are oxidatively dimerized using a procedure previously described in the U.S. Pat. No. 5,120,412, issued Jun. 9, 1992. One of the compounds being dimerized may be emodin anthrone, or emodin anthrone in which the methyl group is replaced by another alkyl group, in order to obtain compounds in which one of $R^1$ and $R^2$ is alkyl. In this case the resulting mixed dimers may be separated by separating techniques which would be well-known to those of ordinary skill in the art.

The dimerization involves heating a solution of the esters in pyridine containing piperidine in the presence of pyridine-N-oxide and catalytic amounts of ferrous sulfate. As a result of this procedure, protohypericin analogs are formed, which on irradiation with visible light are converted, respectively, to the methyl ester (Formula I, $R^1, R^2 =COOCH_3$), propyl ester (Formula I, $R^1, R^2—COOC_3H_7$), butyl ester (Formula I, $R^1, R^2=COOC_4H_9$), 2-methoxyethyl ester (I, $R^1, R^2=COO(CH_2)_2OCH_3$), and 2-(2-methoxyethoxy)ethyl ester (Formula I, $R^1, R^2=COO$ $(CH_2)_2O(CH_2)_2OCH3$).

It was stated in Tang et al., *Antiviral Res.* 13:313 (1990) that hypericin is not active against non-enveloped viruses such as polio and rhino viruses. It was also observed that the antiviral activity of hypericin is considerably enhanced on exposure to light (J. B. Hudson et al., *Antiviral Res.* 15:101 (1991); I. Lopez-Bazzocchi, *Photochem.-Photobiol.* 54:95 (1991)). It was postulated that this photodynamic activity may be related to the photogeneration of singlet oxygen.

Based on these previous observations, we deduced that the ability of hypericin analogs to produce singlet oxygen when bound to liposomes, which mimic in this aspect the cell membrane, is essential for antiviral activity.

The generation of singlet oxygen may be established by irradiation with visible light of the said hypericin analogs incubated in liposomes, such as those formed from soya lecithin. Liposomes are a form of membrane whose constituents are present in cell and viral membranes. The binding of hypericin to to liposomes thus mimics its behavior in cell membranes.

We have determined the quantum yields of hypericin and a number of its analogs, as well as of the previously described octahydroxy hypericin (Formula I, $R^1, R^2=OH$).

The quantum yields of the singlet oxygen formed on irradiation of hypericin, or hypericin analogs in which methyl groups are replaced by esters of carboxylic acid, were comparatively high, while irradiation of octahydroxy or dicarboxylic acid analogs did not produce detectable yields of singlet oxygen, as will be shown in detail in the following example and particularly in Table I.

According to the present invention, the hypericin analogs which show high binding to liposomes and also generate, on irradiation, singlet oxygen in high yield, possess antiviral activity which is correlated to the quantum yield of singlet oxygen and, in many cases, may have an advantage over that of hypericin. In particular, such hypericin analogs consist of compounds in which the two methyl groups of hypericin are replaced by any of various esters of carboxylic acid.

Accordingly, those of ordinary skill in the art can readily determine if any given hypericin analog within the generic formula of the present invention has antiviral activity by subjecting it to the simple physical test for binding to liposomes and singlet oxygen generation upon irradiation. Only those which bind well to liposomes and generate singlet oxygen in high yield will be expected to have antiviral and antiretroviral activity and to thus fall within the scope of the present invention.

The antiviral compounds of the present invention can be used to substantially reduce or completely abolish the infectivity of viruses and retroviruses, and HIV in particular, that may be present in mammals, such as humans, in samples of biological fluids, or on surfaces which have come into contact with such viruses or retroviruses. This termination or reduction in infectivity is accomplished without causing significant interference with most of the routine clinical laboratory tests performed on such samples. The antiviral agents employed to inactivate the virus or retrovirus accomplish this function without rendering blood or blood products toxic or otherwise useless for transfusion or administration to mammals. It is anticipated that the antiviral compounds of the present invention will not interfere with the performance of ELISA (enzyme linked immunosorbent assay) and Western blot assays used to detect antibodies to HIV present in biological fluids such as urine and serum since the antiviral compounds of the present invention do not have any significant effect on the usual constituents of mammalian blood or on blood chemistry. The presence of the antiviral compounds of the present invention are not expected to affect the structural or mechanical properties (e.g., tensile strength) of the materials (e.g., glass, plastic, etc.) used in the construction of containers and devices employed for holding, handling, storing or processing biological fluids or cause any other adverse activity (e.g., reactivity with the biological fluid or container, etc.).

As used herein, inactivation of a virus (or retrovirus) refers to substantially reducing or eliminating the ability of the virus to infect mammalian cells. Such inactivation refers to free virions as well as newly budding virus particles and also to propagation of infection by cell fusion. Thus, an effective amount for inactivating a virus (or retrovirus) of antiviral compounds of the present invention is an amount that will eliminate the ability of a virus (or retrovirus) to infect and/or invade mammalian cells.

Antiviral compounds of the present invention may be incorporated into (or used to clean and disinfect) articles such as containers, receptacles, vacuum bags, blood bags, syringes, needles, tubing and other medical or laboratory devices and equipment used for the collection, retention, storage, processing, handling or testing of biological fluids. Antiviral compounds of the invention may also be employed to inactivate HIV, and other retroviruses (as well as viruses) in human blood products, e.g., as used for transfusion, by incorporating the compounds directly into articles and devices, such as flexible plastic bags, used to store and transfuse blood. In another application, the antiviral compounds of the present invention are used with male and female contraceptive devices, as well as compositions, to inactivate HIV and other retroviruses and viruses present in semen or vaginal fluid, thus inhibiting sexual transmission of infections due to such viruses.

The methods and means of using the compounds of the present invention are the same as described in detail in U.S. Pat. No. 5,149,718 for other hypericin analogs. The entire disclosure of U.S. Pat. No. 5,149,718, and particularly column 3, line 58, through column 11, line 3, thereof, are hereby incorporated herein by reference. It should be noted that the antiviral and antiretroviral activity of the hypericin analogs of the present invention could not have been predicted from the disclosure of U.S. Pat. No. 5,149,718 as such compounds are not specifically mentioned or even covered by any generic formulas of that patent. The activity of the compounds of the present invention is particularly unexpected in view of the inactivity of the free carboxylic acid analog.

The antiviral compounds of the present invention may be administered in the same manner and in the same pharmaceutical formulations as have already been disclosed for hypericin. Thus, for a pharmaceutical composition, any pharmaceutically acceptable excipient may be used with the active principle. For example, the excipients may be those commonly used for oral, parenteral, topical, aerosol, etc., application. The administration forms, pharmaceutical preparations, dosages, etc. disclosed for example in U.S. Pat. No. 4,898,891 at column 5, line 44, through column 7, line 45, and in U.S. Pat. No. 5,047,435 at column 4, line 55, through column 6, line 46, are hereby incorporated herein by reference.

The present invention is described further below in specific working examples which are intended to illustrate the invention, without limiting its scope.

All patent applications, patents and literature references referred to in this specification are hereby incorporated by reference in their entirety.

EXAMPLE 1

Synthesis of Methyl Ester Analog of Hypericin (Formula I, $R^1$, $R^2$=COOCH$_3$).

a) Emodic Acid Anthrone Methyl Ester.

Emodic acid anthrone, 0.1 g, was dissolved in 50 ml of methanol containing 0.1 ml of conc. sulfuric acid. The solution was refluxed for 4 hours and then neutralized with sodium bicarbonate and evaporated to dryness and the residue crystallized to give the methyl ester of emodic acid anthrone; MS: M 300.26 $C_{16}H_{12}O_6$; IR (KBr) 1703, 1638, 1622, 1602, 1561, 1488, 1435, 1393, 1359, 1286, 1230, 1175, 1160, 1062, 766 cm$^{-1}$; H-NMR (DMSO) 3.90 (3H,s), 4.46 (2H,m), 6.29 (1H,t,J=2Hz), 6.46 (1H,t,J=2Hz), 7.30 (1H,s), 7.50 (1H,s), 11.0 (1H,s,OH), 12.2 (1H,s,OH), 12.3 (1H,s,OH).

b) Methyl Ester Analog of Hypericin.

Methyl ester of emodic acid anthrone, 1 g, was dissolved in a mixture of 20 ml pyridine and 4 ml piperidine. To the resulting solution were added 2 g of pyridine N-oxide, and 0.1 g ferrous sulfate heptahydrate, and the reaction mixture refluxed for 3 hours at 100° C. The mixture was concentrated under vacuum and the residue chromatographed over silica gel column. The violet colored fractions containing the respective protohypericin analog eluted with a mixture of ethyl acetate and methanol (8:2), were irradiated with a halogen lamp of 100 Watts for 2 hours. During this time the color of the fractions changed to red, and in the UV visible absorption spectrum a peak appeared at 590 nm. These fractions were then combined, evaporated to dryness and rechromatographed over silica gel column, and eluted with the same solvent mixture as above, to give the methyl ester of hypericin analog. IR (KBr) 1710, 1581, 1560, 1506, 1463, 1428, 1374, 1341, 1284, 1232, 1178, 1110, 998, 933, 836, 771 cm$^{-1}$; H NMR (DMSO) γ7.55 (1H,s), 6.50 (1H,s), 3.77 (3H,s) ppm; UV vis (EtOH) 593, 550, 479, 379, 328 nm (42,000, 22,000, 15,000, 12,000, 31,000).

EXAMPLE 2

Synthesis of n-propyl Ester Analog of Hypericin (Formula I, $R^1$, $R^2$=COOC$_3$H$_7$).

a) Propyl Ester of Emodic Acid Anthrone.

Emodic acid anthrone, 0.1 g, was dissolved in 20 ml of propanol containing 0.1 ml of conc. sulfuric acid, neutralized with sodium bicarbonate, and evaporated to dryness to give the title compound, 0.6 g. MS M 328.1 C$_{18}$H$_{16}$O$_6$; IR (KBR) 1719, 1604, 1488, 1472, 1385, 1377, 1286, 1230, 1170, 1061, 915, 804, 771 cm$^{-1}$.

b) N-propyl ester analog of hypericin.

Propyl ester of emodic anthrone, 0.1 g, was dissolved in a mixture of 10 ml pyridine and 2 ml piperidine containing 1 g of pyridine N-oxide, and 0.5 g ferrous sulfate heptahydrate were added, and then treated as described in Example 1 (b), to give the respective protohypericin analog which was converted by irradiation to the propyl ester analog of hypericin. The pure compound was isolated after chromatography on silica gel. IR (KBr) 1632, 1700, 1588, 1553, 1463, 1420, 1397, 1221, 1113, 1062, 848, 668 cm$^{-1}$; UV-vis (EtOH) 593.5, 550, 480, 379, 327 nm. (42,000, 23,000, 15,000, 13,000, 30,000); H-NMR (MeOH) 0.82 (3H,t,J-7 Hz), 1.57 (2H,m), 4.10 (2H,m), 7.42 (1H,s) ppm.

EXAMPLE 3

Synthesis of n-butyl Ester Analog of Hypericin (Formula I, $R^1$, $R^2$—COOC$_4$H$_9$).

a) Emodic Acid Anthrone n-butyl Ester.

Emodic acid anthrone, 0.12 g, was dissolved in 50 ml of n-butanol containing 0.1 ml of conc. sulfuric acid. The solution was refluxed for 4.5 hours and then neutralized with sodium bicarbonate and evaporated to dryness. Crystallization from propan-2-ol gave 0.6 g of the title compound, Mp. 129–132°.

b) N-butyl Ester of Hypericin Analog.

The above material, 0.1 g, was dissolved in a mixture of 5 ml pyridine and 1 ml piperidine containing 0.6 g of pyridine N-oxide, and 0.1 g ferrous sulfate heptahydrate, and then treated as described under Example 1 (b) to give the respective protohypericin analog which was converted by irradiation to the n- butyl ester analog of hypericin.

EXAMPLE 4

Synthesis of 2-Methoxyethyl Ester Analog of Hypericin
(Formula I, $R^1$, $R^2$=COOCH$_2$CH$_2$OCH$_3$)

a) Emodic Acid Anthrone 2-Methoxyethyl Ester.

Emodic acid anthrone, 0.5 g, was dissolved in 10 ml of Methyl Cellosolve (2-methoxyethanol) containing 0.1 ml of conc. sulfuric acid. The solution was refluxed for 4.5 hours and then neutralized with sodium bicarbonate and evaporated to dryness. Crystallization from methanol gave 0.3 g of the title product.

b) 2-Methoxyethyl Ester of Hypericin Analog.

The above material, 0.1 g, was dissolved in a mixture of 5 ml and 1 ml piperidine. To the resulting solution were added 0.5 g of pyridine N-oxide, and 0.01 g ferrous sulfate heptahydrate, and then treated as described under Example 1 (b) to give the respective protohypericin analog which was converted by irradiation to the 2-methoxyethyl ester analog of hypericin. The pure compound was isolated after chromatography on silica gel. It consisted of the n-butyl ester of hypericin analog (Formula I, $R^1$, $R^2$, COOC$_4$H$_9$). Uv-vis 598, 553, 486 nm (33,000, 13,000, 10,000).

EXAMPLE 5

Synthesis of 2-(2-Methoxyethoxy)ethyl Ester Analog of Hypericin
(Formula I, $R^1$, $R^2$=COOCH$_2$CH$_2$OCH$_2$CH$_2$OCH$_3$ a) Emodic Acid Anthrone 2-(-2-Methoxyethoxy)ethyl Ester.

Emodic acid anthrone, 0.12 g, was dissolved in 50 ml of n-butanol containing 0.1 ml of conc. sulfuric acid. The solution was refluxed for 4.5 hours and then neutralized with sodium bicarbonate and evaporated to dryness to give the title compound.

b) 2-(2-Methoxyethoxy)ethyl Ester of Hypericin Analog.

The above material, 0.1 g, was dissolved in a mixture of 5 ml pyridine and 1 ml piperidine containing 0.5 g of pyridine N-oxide, and 0.05 g ferrous sulfate heptahyrdate, and then treated as described under Example 1(b) to give the respective protohypericin which was converted by irradiation to the 2-(2-methoxyethoxy)ethyl ester analog of hypericin. The pure compound was isolated after chromatography on silica gel. UV-vis (EtOH) 594, 550, 480, 378, 328 nm (32,000, 18,000, 13,000, 10,000, 25,000).

EXAMPLE 6

Determination of Antiretroviral Activity of Hypericin Analogs by Monitoring the Direct Inactivation of Murine Radiation Leukemia Virus (Rad LV) Measured by the Inhibition of Virus Particle Derived Reverse Transcriptase Activity Virus particles released into the growth medium of the AQR lymphoblastoid cell line which is infected with and producing RadLV, were exposed to hypericin and hypericin analogs. The virus and the substrate were incubated on ice for a period of 30 min., after which time the virus was precipitated by ultracentrifugation at 40,000 rpm for 1 hour in a Beckman ultracentrifuge, and analyzed for reverse transcriptase according to Stephenson et al., Virology 48:749 (1972). The results shown in FIG. 1 are expressed as counts per minute of tritiated-thymidine incorporation. It was found that at the levels of 0.01 μg/ml, the methyl, and butyl esters of Examples 1 to 3 have shown antiviral activity.

EXAMPLE 7

Antiretroviral Activity of Hypericin Analogs Against Murine Friend Virus in BALB/c Mice Mice infected with Friend virus (FV) develop a virus induced erythroleukemia whose early manifestation is a 4–8 time enlargement of the spleen size (splenomegaly) within 10 days after infection with the virus. Inhibition of splenomegaly can be used to quantitate the antiretroviral activity of various compounds in vivo. In this experiment, mice, in groups of 3, were infected with Friend virus and hypericin analogs (0.5 ml of solution in PBS) were then administered intravenously within 1 hour of the infection in a single dose of 1, 10, 50 and 150 μg per mouse.

The results in FIG. 2 show that the tested hypericin analogs inhibit splenomegaly of Friend-virus infected mice at doses ranging at between 10–150 μg per mouse. At dose levels of 10 μg per mouse, the methyl ester of Example 1 and propyl ester of Example 2 inhibit splenomegaly by 65 and 47% respectively, while at 150 μg per mouse, butyl ester of Example 3 was the most potent of the three compounds tested, showing 70% of inhibition.

EXAMPLE 8

Quantum Yield of Single Oxygen Formation on Irradiation of Hypericin and Hypericin Analogs in Liposomes Saturated dispersions of diphenylisobenzofurane (DPBF) in aqueous soya liposomes (5%), and of hypericin in water were prepared. These dispersions were diluted with water to give concentrations of both DPBF and hypericin having optical density of ca. 1 in the UV-vis spectrum in a 1 cm cell, at wavelengths maxima of 420 nm (DPBF) and 590 nm (hypericin). Aliquots of these two solutions were taken and mixed in the absence of light, and then exposed to light of 420 nm, and the absorption determined at this wavelength, at time 0 and at intervals of 30 seconds for ca. 10 minutes, after which the OD at 420 nm decreased to half its value. The quantum yields of singlet oxygen formation were then established using the procedure described by Gorman et al. J. Amer. Chem. Soc. 100:4527 (1978).

The same procedure was repeated for the above-mentioned methyl and methoxyethyl ester analogs, as well as the octahydroxy and dicarboxy analogs of hypericin. The results of the measurements are depicted in Table I, which shows that the quantum yield of singlet oxygen produced by hypericin and its analogs, in which the methyl groups are replaced by carboxy ester groups, have comparatively high values, while the other hypericin analogs, in which methyl groups are replaced by hydroxy or carboxy groups, did not produce measurable amounts of singlet oxygen. This corresponds well with the antiviral activity shown in the present examples, or otherwise known as discussed above.

TABLE I

Quantum yields of singlet oxygen ($\phi_A$) formed on irradiation of hypericin analogs in liposomes

| Compound Formula I | $\phi_A$ |
|---|---|
| $R_1, R_2 = COOCH_3$ | 0.38 |
| $R_1, R_2 = COOCH_2CH_2OCH_3$ | 0.35 |
| $R_1, R_2 = CO(OCH_2CH_2)_2OCH_3$ | 0.1 |
| $R_1, R_2 = COOH$ | <0.01 |
| $R_1, R_2 = OH$ | <0.01 |

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

We claim:
1. A compound having the structure:

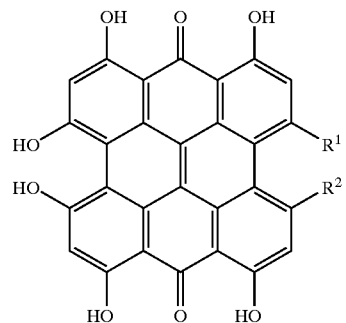

wherein $R^1$ and $R^2$ are carboxylic acid ester group of the formula $COOR^3$, in which $R^3$ is alkyl, the chain of which is optionally interrupted by one or more oxygen or sulfur atoms.

2. A compound in accordance with claim 1, wherein $R^3$ has a total of eight or fewer carbon atoms.

3. A compound in accordance with claim 1, wherein $R^3$ has a total of five or fewer carbon atoms.

4. A compound in accordance with claim 1, wherein $R^3$ has a total of three or fewer carbon atoms.

5. A compound in accordance with claim 1, wherein $R^3$ is selected from the group consisting of methyl, ethyl, propyl, butyl, 2-methoxyethyl, or 2-(2-methoxyethoxy)ethyl.

6. A pharmaceutical composition having antiviral or antiretroviral activity comprising an effective amount of a compound in accordance with claim 1 and a pharmaceutically acceptable excipient.

7. A pharmaceutical composition having antiviral or antiretroviral activity comprising an effective amount of a compound in accordance with claim 2 and a pharmaceutically acceptable excipient.

8. A pharmaceutical composition having antiviral or antiretroviral activity comprising an effective amount of a compound in accordance with claim 3 and a pharmaceutically acceptable excipient.

9. A pharmaceutical composition having antiviral or antiretroviral activity comprising an effective amount of a compound in accordance with claim 4 and a pharmaceutically acceptable excipient.

10. A pharmaceutical composition having antiviral or antiretroviral activity comprising an effective amount of a compound in accordance with claim 5 and a pharmaceutically acceptable excipient.

11. A composition in accordance with claim 6, wherein said compound has the properties of binding well to liposomes and generating a high yield of singlet oxygen when such bound liposomes are subjected to irradiation.

12. A method for the treatment of viral or retroviral diseases comprising administering to a subject having such a disease an effective amount of a compound in accordance with claim 1.

13. A method for the treatment of viral or retroviral diseases comprising administering to a subject having such a disease an effective amount of a compound in accordance with claim 2.

14. A method for the treatment of viral or retroviral diseases comprising administering to a subject having such a disease an effective amount of a compound in accordance with claim 3.

15. A method for the treatment of viral or retroviral diseases comprising administering to a subject having such a disease an effective amount of a compound in accordance with claim 4.

16. A method for the treatment of viral or retroviral diseases comprising administering to a subject having such a disease an effective amount of a compound in accordance with claim 5.

17. A method in accordance with claim 12, wherein said compound has the properties of binding well to liposomes and generating a high yield of singlet oxygen when such bound liposomes are subjected to irradiation.

18. A method for significantly reducing or completely eliminating the infectivity of a virus or retrovirus, comprising contacting said virus or retrovirus with an effective amount of at least one compound in accordance with claim 1.

19. A method in accordance with claim 18 for significantly reducing or completely eliminating the infectivity of a virus or retrovirus present in a retaining means for retaining a biological fluid wherein said contacting step comprises contacting said retaining means with an effective amount of said at least one compound.

20. A method in accordance with claim 18 for significantly reducing or completely eliminating the infectivity of any retrovirus which may be present on a non-biological surface after such surface has come into contact with the biological fluid contaminated with a virus or retrovirus, wherein said contacting step comprises contacting said surface with an effective amount of said at least one compound.

21. A method for treating a surface intended to come into contact with a biological fluid which is infected with a virus or retrovirus in order to significantly reduce or completely eliminate the infectivity of any virus or retrovirus which comes into contact with such surface, comprising placing onto said surface an effective amount of at least one compound in accordance with claim 1.

22. A composition of matter, comprising a spermicidal agent and an antiviral effective amount of at least one compound in accordance with claim 1.

23. A composition of matter comprising a biological fluid and an antiviral effective amount of at least one antiviral compound in accordance with claim 1.

24. A composition of matter, comprising a vaginal lubricating agent and an antiviral effective amount of at least one antiviral compound in accordance with claim 1.

25. An article of manufacture, comprising:
a surface for contacting a biological fluid which may be contaminated with a virus, and
an effective amount for inactivating said virus of at least one antiviral compound having the structure:

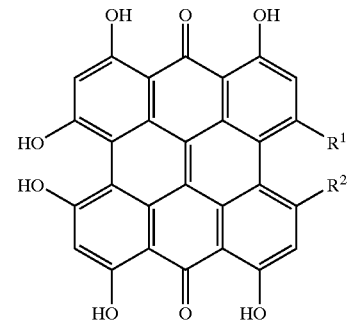

wherein $R^1$ and $R^2$ are carboxylic acid ester groups of the formula $COOR^3$, in which $R^3$ is alkyl, the chain of which is optionally interrupted by one or more oxygen or sulfur atoms, wherein said compound is disposed on said surface to contact said fluid no later than when said fluid contacts said surface.

26. An article according to claim 25 wherein said surface is the internal surface of a condom.

27. An article of manufacture, comprising:

means for retaining a biological fluid; and an antiviral effective amount of at least one antiviral compound having the structure:

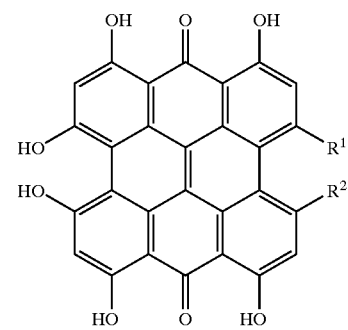

wherein $R^1$ and $R^2$ are carboxylic acid ester groups of the formula $COOR^3$, in which $R^3$ is alkyl, the chain of which is optionally interrupted by one or more oxygen or sulfur atoms, wherein said at least one compound is disposed with respect to said retaining means such that it comes into antiviral contact with the fluid when the fluid is retained in said means.

28. An article of manufacture, comprising:

a container for holding a biological fluid which may be contaminated with a virus, and an effective amount for inactivating said virus of at least one antiviral compound having the structure:

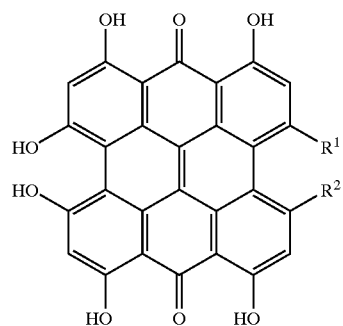

wherein $R^1$ and $R^2$ are carboxylic acid ester groups of the formula $COOR^3$, in which $R^3$ is alkyl, the chain of which is optionally interrupted by one or more oxygen or sulfur atoms, wherein said compound is present in said container so as to contact the fluid when the fluid is introduced into said container.

29. An article of manufacture in accordance with claim 28 wherein said container is selected from the group consisting of a blood bag, a blood vacuum storage tube, a condom, a test tube, and a urine cup.

* * * * *